United States Patent
Nabeshima (10) Patent No.: US 10,598,571 B2
(45) Date of Patent: Mar. 24, 2020

(54) PERFORMANCE EVALUATION APPARATUS AND PERFORMANCE EVALUATION METHOD FOR WEARABLE MOTION ASSISTANCE DEVICE

(71) Applicant: CYBERDYNE INC., Tsukuba-shi, Ibaraki (JP)

(72) Inventor: Kota Nabeshima, Ibaraki (JP)

(73) Assignee: CYBERDYNE INC., Tsukuba-shi, Ibaraki (JP)

( * ) Notice: Subject to any disclaimer, the term of this patent is extended or adjusted under 35 U.S.C. 154(b) by 38 days.

(21) Appl. No.: 16/065,741

(22) PCT Filed: Dec. 21, 2016

(86) PCT No.: PCT/JP2016/088219
§ 371 (c)(1),
(2) Date: Jun. 22, 2018

(87) PCT Pub. No.: WO2017/110930
PCT Pub. Date: Jun. 29, 2017

(65) Prior Publication Data
US 2019/0011330 A1  Jan. 10, 2019

(30) Foreign Application Priority Data

Dec. 22, 2015  (JP) ................. 2015-250686

(51) Int. Cl.
*G01M 99/00* (2011.01)
*A61H 3/00* (2006.01)

(52) U.S. Cl.
CPC ............ *G01M 99/007* (2013.01); *A61H 3/00* (2013.01); *G01M 99/005* (2013.01); *A61H 2201/165* (2013.01)

(58) Field of Classification Search
CPC ..... G01M 99/005; G01M 99/007; G01L 3/00; G01L 3/1492; G01L 5/0042; G01L 25/00;
(Continued)

(56) References Cited

U.S. PATENT DOCUMENTS

2005/0166685 A1* 8/2005 Boiten ...................... A61F 2/68
73/862.191
2006/0276728 A1* 12/2006 Ashihara ............... A61F 5/0102
601/5
(Continued)

*Primary Examiner* — Benjamin R Schmitt
(74) *Attorney, Agent, or Firm* — Procopio, Cory, Hargreaves & Savitch LLP (57) ABSTRACT

A performance evaluation apparatus and performance evaluation method capable of efficiently evaluating the performance of a wearable motion assistance device is provided, which assists motions of a wearer's lower back part. In a state where the wearable motion assistance device is secured and mounted on both femur links and a trunk link, torque acting on an axis line of a pitch direction relative to the trunk link for each hip joint is detected while controlling driving forces by first and second driving sources so that a posture of the trunk link and rotation angles of each hip joint and each knee joint virtually match motions of the lower back part of the wearer; and performance of an assist force by the wearable motion assistance device is evaluated based on a detection result of the torque according to drive control of the first and second driving sources.

12 Claims, 8 Drawing Sheets

(58) Field of Classification Search
CPC ................. A61H 3/00; A61H 2201/16; A61H 2201/1623; A61H 2201/165; A61H 2201/50; A61H 2201/5058; A61H 2201/5061
USPC ................ 73/862.08, 862.191, 865.4, 865.9; 623/27, 30, 31, 912
See application file for complete search history.

(56) References Cited

U.S. PATENT DOCUMENTS

| | | | | |
|---|---|---|---|---|
| 2008/0255488 | A1* | 10/2008 | Agrawal | A63B 21/00181 602/23 |
| 2010/0324699 | A1* | 12/2010 | Herr | A61F 2/66 623/27 |
| 2013/0158444 | A1* | 6/2013 | Herr | A61H 1/0255 601/23 |

* cited by examiner

PERFORMANCE EVALUATION APPARATUS AND PERFORMANCE EVALUATION METHOD FOR WEARABLE MOTION ASSISTANCE DEVICE

CROSS-REFERENCE TO RELATED APPLICATIONS

This application is a U.S. National Stage entry of PCT Application No: PCT/JP2016/088219 filed Dec. 21, 2016, which claims priority to Japanese Patent Application No. 2015-250686, filed Dec. 22, 2015, the contents of which are incorporated herein by reference.

TECHNICAL FIELD

The present invention relates to a performance evaluation apparatus and performance evaluation method for a wearable motion assistance device. Particularly, the invention is suited for application in an apparatus for objectively evaluating the performance of a motion assistance device that assists motions of a wearer's lower back part.

BACKGROUND ART

In recent years, various power assist devices have been being developed to assist or substitute motions of physically handicapped persons, elderly persons, and/or healthy persons in daily life or during work. An example of a wearable electromechanical device for power assist is a wearable motion assistance device to be worn by a user (hereinafter referred to as the "wearer").

The wearable motion assistance device: includes, as a means for detecting inputs by the wearer, a conventional operating device composed of buttons and switches, and sensors for detecting the wearer's body weight movements, movements of their body, a biological signal, sounds, and gestures; and also includes a control means for generating a command signal (control signal) for causing a driving source to generate motive power (assist force) according to such inputs (for example, NPL 1).

CITATION LIST

Non-Patent Literature

NPL1: Takao Nakai, Suwoong Lee, Hiroaki Kawamoto and Yoshiyuki Sankai, "Development of Power Assistive Leg for Walking Aid using EMG and Linux," Second Asian Symposium on Industrial Automation and Robotics, BITECH, Bangkok, Thailand, May 17-18, 2001

SUMMARY OF THE INVENTION

Problems to be Solved by the Invention

Meanwhile, wearable motion assistance devices like the one described above has been released particularly recently by many manufacturers; and those wearable motion assistance devices for livelihood support can be further classified into those for work support and those for care support and there are many types of drive systems such as an electrically-driven type and a hydro-pneumatic drive type.

Therefore, regardless of who the manufacturers are, objective standards are required to integrally evaluate the performance of the wearable motion assistance devices for the lower back assistance.

However, when the wearer in the state wearing the wearable motion assistance device performs a sequence of motion patterns such as holding and lifting down a package, keeping their posture, and lifting up the package, there has never existed an apparatus that evaluates, for example, how much assist force is generated on right and left knee joints and right and left hip joints at which timing, uniformly with respect to the relevant products regardless of the types of the products.

When actually constructing a performance evaluation apparatus, it is necessary to evaluate not only the assist force for bending and extending each joint of both legs, but also the performance regarding the degree of adduction/abduction range of motion of the hip joints. So, it can be anticipated that it will be very cumbersome and complicated to construct the performance evaluation apparatus.

Therefore, the performance evaluation apparatus should preferably be constructed so that the same apparatus is used to enable easy evaluation of the performance with respect to the assist force for bending and extending leg joints and the adduction/abduction range of motion of the hip joints.

The present invention was devised in consideration of the above-described circumstances and provides a performance evaluation apparatus and performance evaluation method capable of efficiently evaluating the performance of a wearable motion assistance device, which assists the motions of the wearer's lower back part, by using a comparatively simple configuration.

Means to Solve the Problems

In order to solve the above-described problems, provided according to the present invention is a performance evaluation apparatus for a wearable motion assistance device to be mounted on a wearer by securing both femoral parts of the wearer and either one or both of an abdominal part and shoulder parts of the wearer to assist motions of a lower back part of the wearer, wherein the performance evaluation apparatus includes: a base with first and second driving sources built therein; right and left knee joints, each of which is connected between the base and a pair of femur links so that each knee joint can rotate freely in a pitch direction with a driving force of the first driving source transmitted to only either one of the knee joints; right and left hip joints, each of which is connected between each femur link and a trunk link so that each hip joint can rotate freely in the pitch direction with a driving force of the second driving source transmitted to only either one of the hip joints; a torque detecting unit that detects torque acting on an axis line of the pitch direction relative to the trunk link for each hip joint; and a control unit that controls the driving forces by the first and second driving sources so that a posture of the trunk link and rotation angles of each hip joint and each knee joint virtually match motions of the lower back part of the wearer, wherein the control unit evaluates performance of an assist force by the wearable motion assistance device on the basis of a detection result of the torque detecting unit according to drive control of the first and second driving sources in a state where the wearable motion assistance device is secured and mounted on both the femur links and the trunk link.

As a result, the first and second driving sources which are built in the base can distribute and transmit the driving force to the knee joint of only one of the pair of femur links (the left side or the right side) and to the hip joint on the other side (the right side or the left side) as active joints; and it is possible to reduce a transmission error occurrence probability as much as possible.

Furthermore, when both the knee joint and the hip joint connected to one femur link (on the left side or the right side) of the pair of femur links are used as the active joints, the installed status of belt driving inside the knee joint and the hip joint may become complicated and may possibly cause any defects by interfering with each other. So, it is possible to prevent the occurrence of such defects.

Furthermore, according to the present invention, in the state where the wearable motion assistance device is secured and mounted on both the femur links and the trunk link, the control unit judges whether or not a braking force of a predetermined level is generated upon the occurrence of a malfunction or a failure of the wearable motion assistance device, on the basis of a detection result of the torque detecting unit in accordance with drive control of the first and second driving sources.

As a result, if the wearable motion assistance device does not generate the braking force of the predetermined level upon the occurrence of a malfunction or failure, the wearable motion assistance device can be evaluated as unacceptable.

Furthermore, according to the present invention, at least one of the respective hip joints can rotate in a rolling direction relative to the femur link and the connection with the base at the femur link can be released; the performance evaluation apparatus further includes, within the apparatus or as separate units: a force component detecting unit that detects a force component acting on an axis line of the rolling direction of the hip joint; and a rotation angle detecting unit that detects a rotation angle of the axis line of the rolling direction of the hip joint; and when an external force is applied in the rolling direction of the femur link in the state where the wearable motion assistance device is secured and mounted on both the femur links and the trunk link, the control unit evaluates performance of an adduction/abduction range of motion by the wearable motion assistance device, on the basis of each detection result of the force component detecting unit and the rotation angle detecting unit.

As a result, it becomes possible to easily evaluate not only the performance of the assist force for bending/extending of the hip joints respectively corresponding to the pair of knee joints, but also the performance of the adduction/abduction range of motion of one hip joint (on the right side or the left side).

Furthermore, according to the present invention, a load detecting unit that is provided at a site in the trunk link corresponding to the lower back part of the wearer and detects a load applied to the site is further included; and in the state where the wearable motion assistance device is secured and mounted on both the femur links and the trunk link, the control unit estimates the load applied to the lower back part of the wearer by the wearable motion assistance device on the basis of a detection result of the load detecting unit in accordance with drive control of the first and second driving sources.

As a result, it becomes possible to judge how much the load applied to the wearer's lower back part by the wearable motion assistance device has been reduced.

Advantageous Effects of the Invention

According to the present invention, a performance evaluation apparatus and performance evaluation method for a wearable motion assistance device can be realized so that the same apparatus can be used to evaluate the entire performance of the device including not only the evaluation of the assist force for bending and extending the leg joints and the performance of the adduction/abduction range of motion of the hip joints, but also estimation of the load applied to the wearer's lower back part.

DESCRIPTION OF EMBODIMENTS

An embodiment of the present invention will be described below in detail with reference to the drawings.

Figure 1:
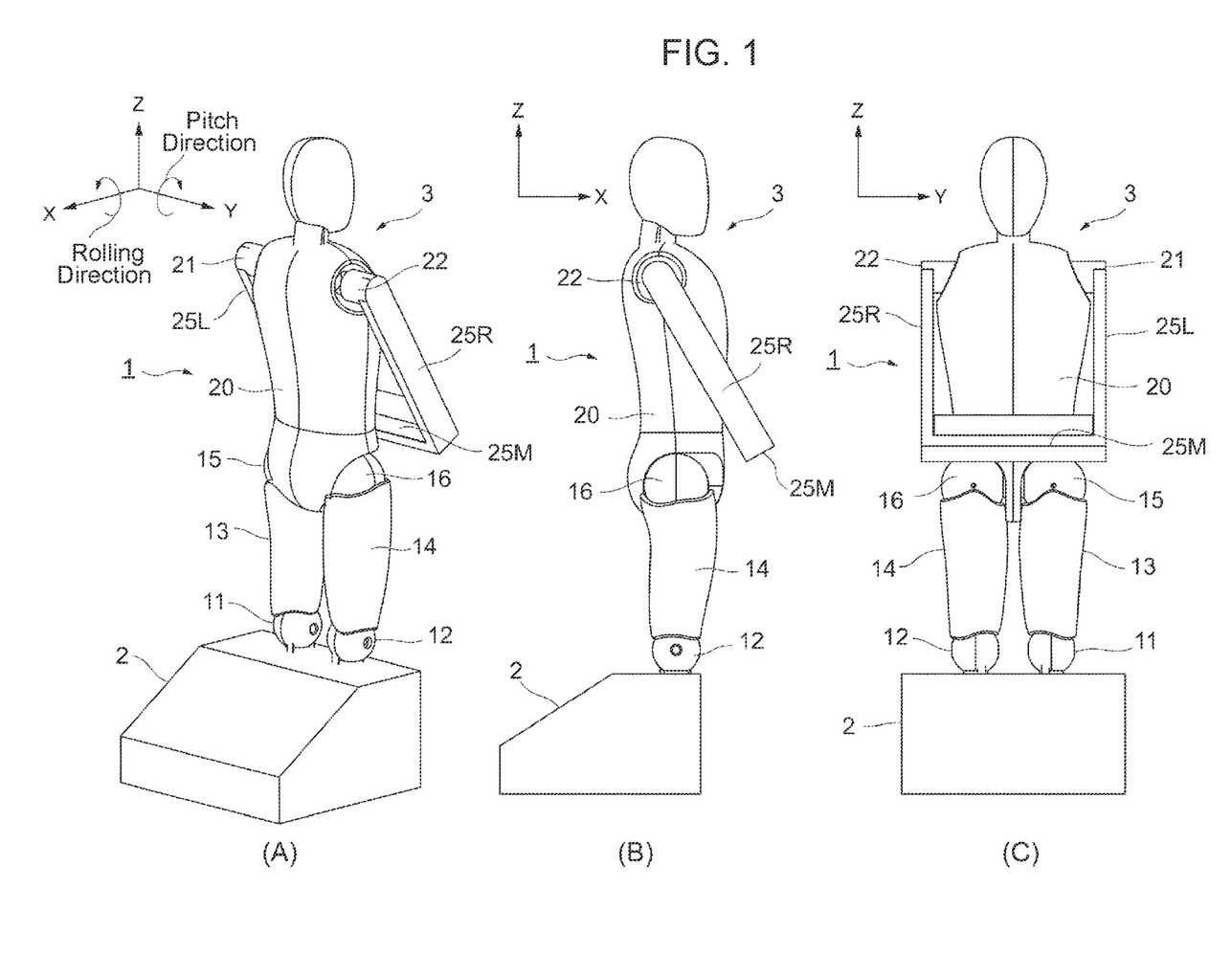
FIG. 1 shows a perspective view, a side view, and a front view which illustrate an appearance configuration of a performance evaluation apparatus according to an embodiment of the present invention.

(1) Configuration of Performance Evaluation Apparatus for Wearable Motion Assistance Device FIG. 1A to FIG. 1C illustrate a performance evaluation apparatus 1 according to this embodiment, which is configured in such a manner that a base 2 installed and secured on a floor surface is used as a basis and a humanoid motion test unit 3 is connected to the top of the base 2 in a freely movable manner.

The humanoid motion test unit 3 has an external shape substantially similar to that of a human body part above their knees and is equipped with a joint mechanism so that a sequence of motions of a human lifting up an object and then lifting it down and thereby imposing a burden on their lower back part can be artificially simulated.

The base 2 for the performance evaluation apparatus 1 is made of a material with relatively heavy weight and is designed so that when each joint is activated, only the humanoid motion test unit 3 operates while being secured on the floor surface 2 even in the state a package or the like is held by arm parts of the humanoid motion test unit 3.

Figure 2:
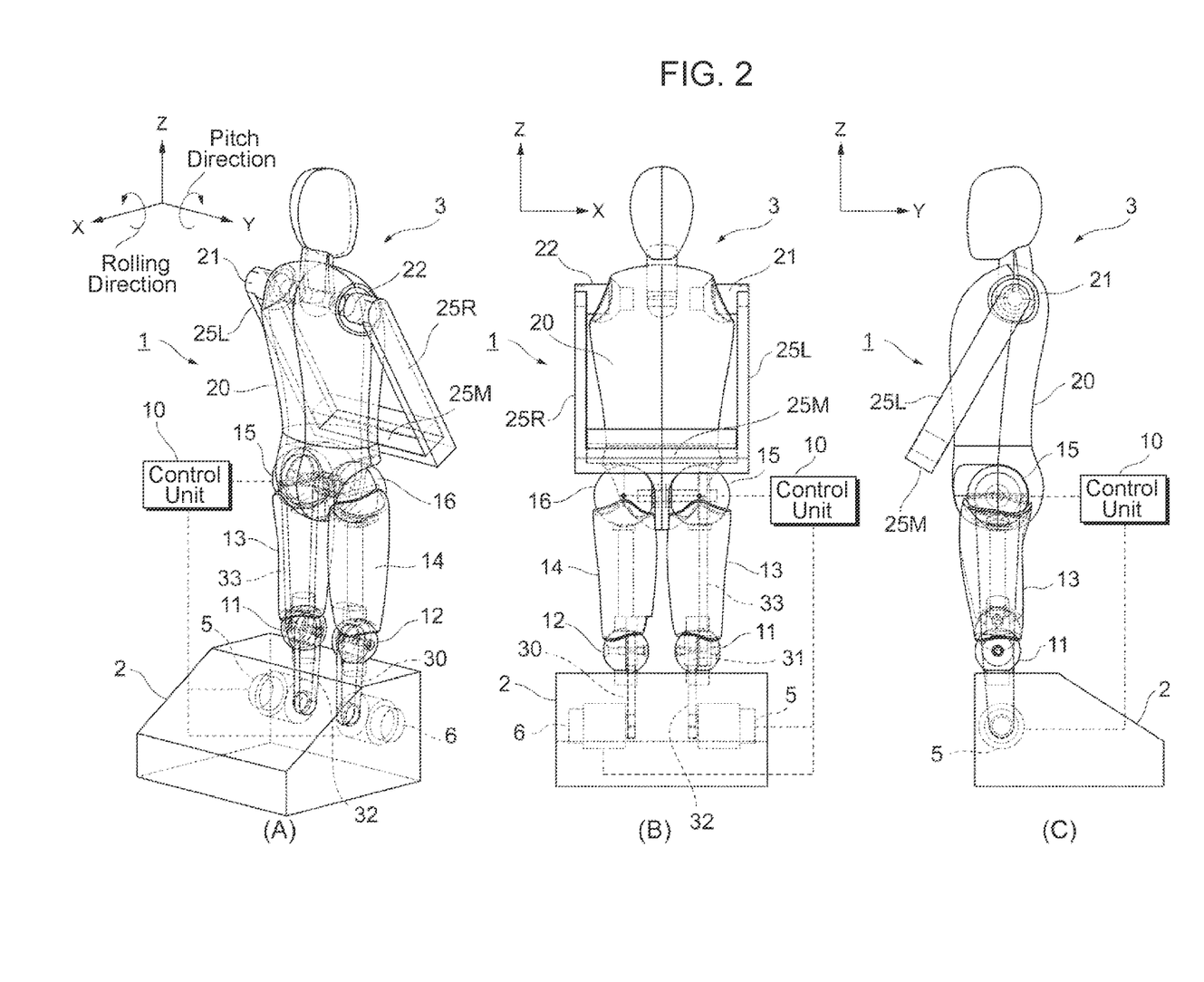
FIG. 2 shows a perspective view, a side view, and a front view which illustrate an internal mechanism system for the performance evaluation apparatus according to the embodiment.

First and second driving sources 5, 6 (FIG. 2) which are electric actuators are respectively built in the base 2 and are drive-controlled in accordance with control by a control unit 10 (FIG. 2). This control unit 10 may be attached to the base 2 or an external personal computer (not shown) may be applied by means of a wireless or wired communication system.

Regarding the performance evaluation apparatus 1, right and left knee joints 11, 12 of the humanoid motion test unit 3 are embedded in the base 2 in such a manner that the knee joints 11, 12 correspond to the first and second driving sources 5, 6, respectively; and a corresponding femur link 13, 14 is connected to each knee joint 11, 12. Then, a trunk link 20 is connected to the right and left femur links 13, 14 respectively via hip joints 15, 16.

The trunk link 20 has an appearance configuration simulating a human's trunk part and head part, which are formed into an integrated body; and arm links 25L, 25R are connected to right and left areas below the head part via shoulder joints 21, 22 in such a manner that the arm links 25L, 25R can freely rotate.

The right and left arm links 25L, 25R are configured to be connected and integrated in a substantially C-shape and their ends are supported by the shoulder joints 21, 22 respectively in such a manner that the arm links 25L, 25R can freely rotate. A load with desired weight can be applied to a central part 25M that is a site where both the arm links 25L, 25R are connected.

The shoulder joints 21, 22 are designed so that a fastening force can be adjusted by, for example, fastening of bolts and a frictional force in the rotating direction can be adjusted. When actually evaluating the performance of the assist force, the frictional force in the rotating direction is adjusted in advance so that both the arm links 25L, 25R can turn vertically downward during operation.

(2) Drive Transmission System for Performance Evaluation of Assist Force

Regarding the performance evaluation apparatus 1 illustrated in FIG. 2A to FIG. 2C, the second driving source 6 is configured to actively drive only the right-side knee joint 12 of the right and left knee joints 11, 12 and the first driving source 5 is configured to actively drive only the left-side hip joint 15 of the right and left hip joints 15, 16.

Each of the right and left knee joints 11, 12 is connected to the femur link 13, 14 so that the knee joint 11, 12 can rotate freely in a pitch direction (around Y-axis); and as the driving force of the second driving source 6 is transmitted to the right-side knee joint 12, both of them rotate in the pitch direction.

Specifically speaking, a belt 30 is placed around an output axis of the second driving source 6 and around a rotation axis of the right-side knee joint 12, so that the driving force of the second driving source 6 is transmitted via the belt 30 to the rotation axis of the right-side knee joint 12.

The right and left hip joints 15, 16 are connected to the trunk link 20 in such a manner that the hip joint 15, 16 can freely rotate in the pitch direction (around Y-axis); and as the driving force of the first driving source 5 is transmitted to the left-side hip joint 15, both of them rotate in the pitch direction.

Specifically speaking, a belt 32 is placed around an output axis of the first driving source 5 and around a dependent roller 31 which is provided in a freely rotatable manner on a rotation axis of the left-side knee joint 11; and the driving force of the first driving source 5 is transmitted via the belt 32 to the dependent roller 31. A belt 33 is placed around the dependent roller 31 and around a rotation axis of a left-side hip joint 15, so that a rotational force transmitted to the dependent roller 31 is transmitted via the belt 33 to the rotation axis of the left-side hip joint 15.

When this happens, the left-side hip joint 15 rotates in the pitch direction along with the rotational drive of the right-side hip joint 16; however, the left-side hip joint 15 is passively driven without the driving force from the first driving source 5 being transmitted to its rotation axis. Specifically speaking, the dependent roller (pulley) 31 which is mounted on the rotational axis of the left-side knee joint 15, together with the placed two belts 32, 33, serves a medium role to transmit the driving force of the first driving source 5 to the rotation axis of the left-side hip joint 15.

Accordingly, an angle of the dependent roller 31 for the left-side knee joint 11 changes depending on an angle of the left-side femur link 13, so that a direction of the belt 33 also changes; and the driving force of the first driving source 5 is transmitted via the dependent roller 31 to the rotation axis of the pitch direction for the left-side hip joint 15.

Figure 3:
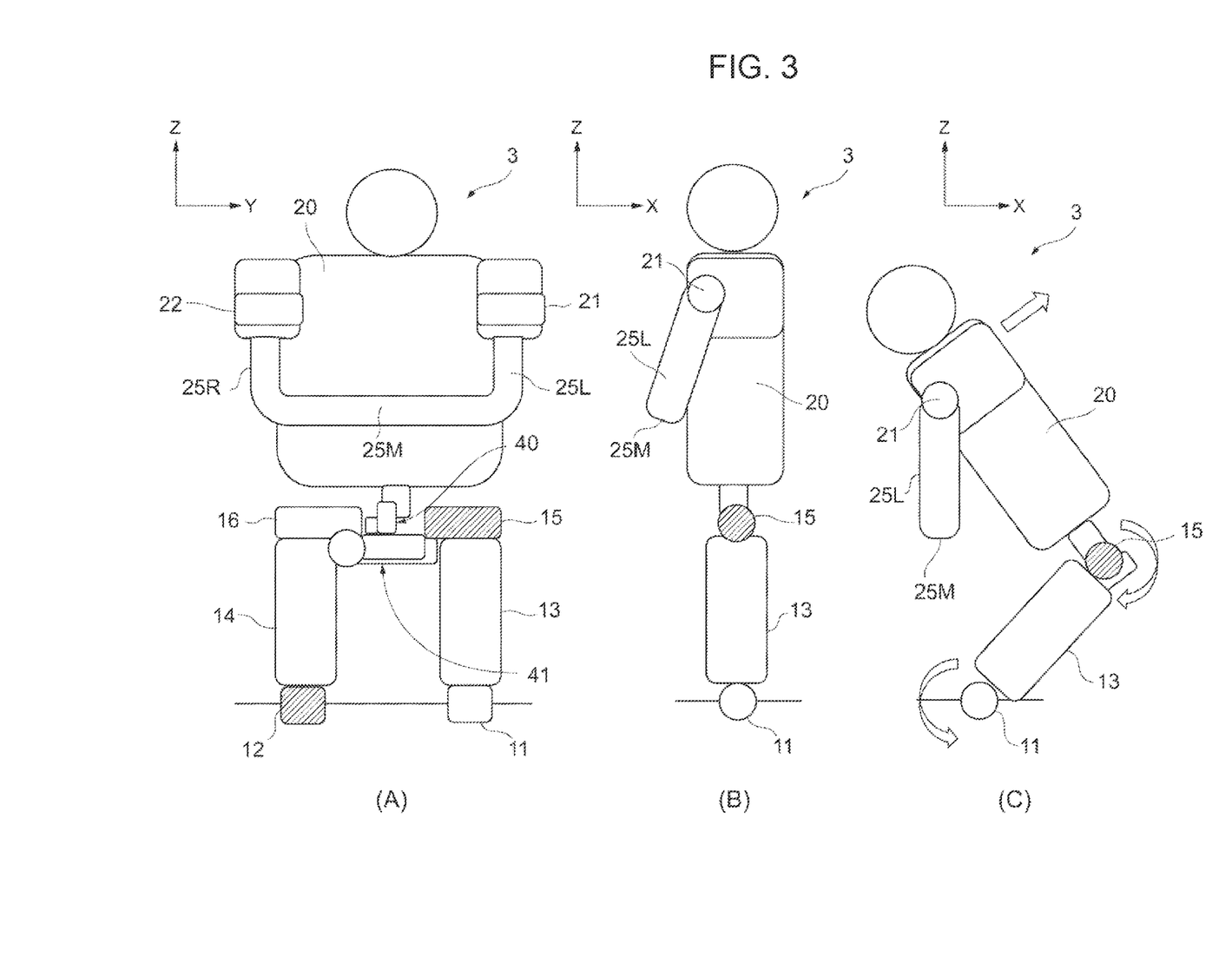
FIG. 3 is a schematic diagram for explaining assist force performance evaluation by the performance evaluation apparatus according to the embodiment.

Referring to FIG. 3A to FIG. 3C, a torque detecting unit 40 for detecting torque which acts on an axis line of the pitch direction relative to the trunk link 20 is provided on the rotation axis of the left-side hip joint 15. This torque detecting unit 40 may be provided on a rotation axis of the right-side hip joint 16. Furthermore, the torque detecting unit 40 may be provided in the base 2 so that the torque detecting unit 40 may detect a current value of a driving current of the first driving source 5 and thereby convert the driving current into a torque value based on the current value.

The control unit 10 rotationally drives the right-side knee joint 12 in the pitch direction and, at the same time, rotationally drives the left-side hip joint 15 in the pitch direction by controlling the driving forces by the first and second driving sources 5, 6 so that the posture of the trunk link 20 and rotation angles of each hip joint 15, 16 and each knee joint 11, 12 virtually match motions of the wearer's lower back part.

Incidentally, a 6-axis force sensor 41 is provided at a part corresponding to a lumbar spine of the trunk link 20 and is designed to detect torque and a 3-axis force applied to any rotation direction of a pitch direction (around Y-axis), rolling direction (around X-axis), and yaw direction (around Z-axis) of the lumbar spine part and transmit the detection result to the control unit 10.

Figure 4:
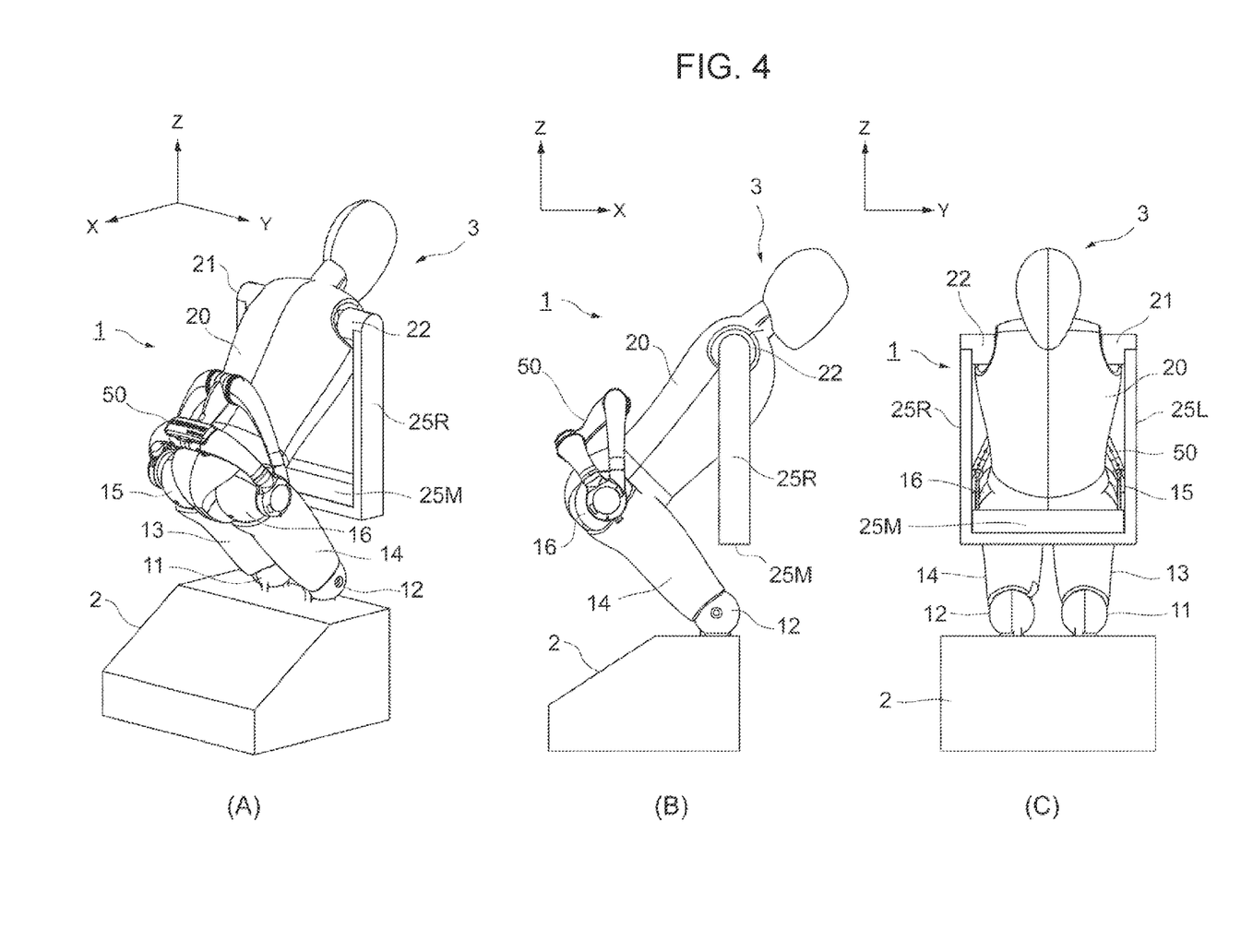
FIG. 4 shows a perspective view, a side view, and a front view in which the wearable motion assistance device is actually mounted on a humanoid motion test unit according to the embodiment.

Practically, as illustrated in FIG. 4A to FIG. 4C, a wearable motion assistance device (see, for example, Japanese Patent Application No. 2014-198655) 50 for assisting the motions of the wearer's lower back part is mounted by securing the wearable motion assistance device 50 to both the femur links 13, 14 and either one or both of the trunk link 20 and the shoulder joints 21, 22 in the humanoid motion test unit 3; and the control unit 10 evaluates the performance of the assist force by the wearable motion assistance device 50 on the basis of the detection result of the torque detecting unit 40 according to the drive control of the first and second driving sources 5, 6.

Incidentally, as a method for evaluating the performance of the assist force, motion patterns of lifting down an object, maintaining the posture, and lifting up the object are defined as one set and the motion patterns are repeated until, for example, 10 sets are completed. Regarding the lift-up motion and the lift-down motion, when a trunk angle reaches a predetermined range of a target angle (for example, −5° or more or less than +5°) within a predetermined range of required time (for example, time in excess of −0.4 s and less than +0.4 s), the relevant motion is terminated and the test proceeds to the next motion. When this condition is not satisfied, the wearable motion assistance device is evaluated as unacceptable and the test is suspended at that moment.

Furthermore, the posture-maintaining motion is performed until a specified amount of required time elapses; and when a joint angle reaches beyond a predetermined range of a target angle (for example, less than −5° or +5° or more) within the above-mentioned time, the wearable motion assistance device is evaluated as unacceptable and the test is suspended at that moment.

In the state the wearable motion assistance device 50 is secured and mounted on both the femur links 13, 14 and the trunk link 20, the control unit 10 judges whether a braking force of a predetermined level is generated upon the occurrence of a malfunction or failure of the wearable motion assistance device 50, on the basis of the detection result of the torque detecting unit 40 according to the drive control of the first and second driving sources 5, 6.

Practically, the wearable motion assistance device 50 has to have a braking function and a lock function to satisfy standards like those described as follows. The wearable motion assistance device 50: (1) is activated in synchronization with the timing when the relevant single disfunction, malfunction, or failure is detected; (2) performs braking for motions of all actuators which generate the assist force; (3) generates the braking force in excess of the maximum assist force within predetermined time (200 ms: response time for a person to exert a sufficient force in response to an acute increase of the load on the lower back part) after the detection; (4) can be released manually by the wearer during operation or can be driven in excess of the braking force; and (5) satisfies the performance level b or higher as defined by ISO 13849-1.

When the motive power supplied to all the actuators which generate the assist force is blocked in the wearable motion assistance device 50, all loads borne by the assist force just before the blocking of the motive power supply will be imposed on the wearer's lower back part. Accordingly, if the brake or the lock can be activated at a sufficiently fast response speed and the braking force exceeds the maximum assist force of the robot, it is believed possible to reduce the load on the lower back part which is attributable to the acute increase of the load.

Figure 5:
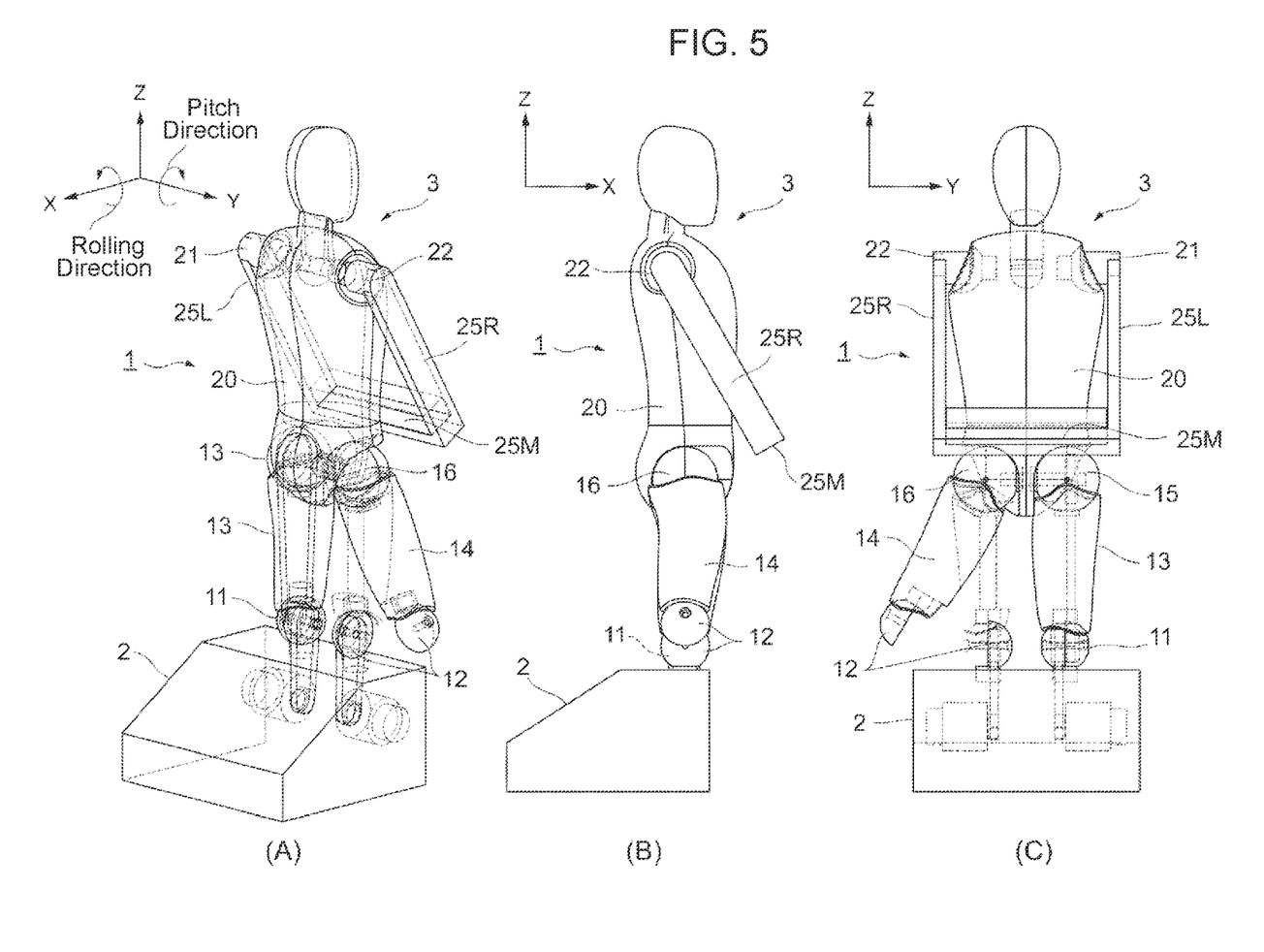
FIG. 5 shows a perspective view, a side view, and a front view which illustrate an appearance configuration of a performance evaluation apparatus according to an embodiment of the present invention.

(3) Drive Transmission System for Performance Evaluation of Adduction/Abduction Range of Motion With the performance evaluation apparatus 1 illustrated in FIG. 5A to FIG. 5C, the right-side hip joint 16 of the right and left hip joints 15, 16 for the humanoid motion test unit 3 is connected to the femur link 14 on not only its rotation axis in the pitch direction (around Y-axis), but also its rotation axis in the rolling direction (around X-axis).

Figure 6:
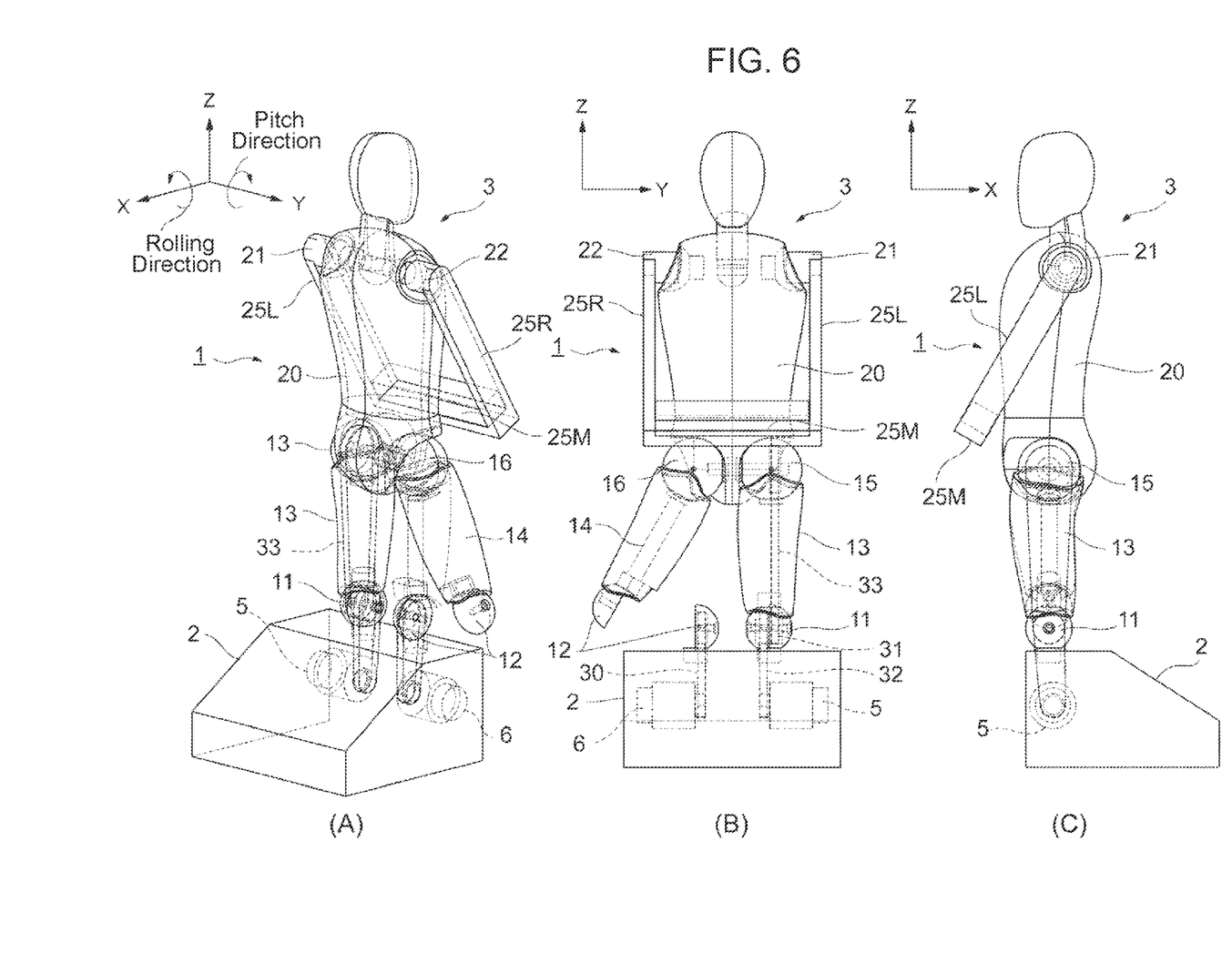
FIG. 6 shows a perspective view, a side view, and a front view which illustrate an internal mechanism system for the performance evaluation apparatus according to the embodiment.

Then, referring to FIG. 6A to FIG. 6C, the right-side knee joint 12 of the right and left knee joints 11, 12 is configured so that part of the right-side knee joint 12 can be separated and moved away while maintaining the state of connection with the output axis of the second driving source 6 (that is, while leaving its active joint part).

Accordingly, the examiner can move the right-side femur link 14 in the rolling direction (adduction/abduction direction) with reference to the relevant knee joint 12 while holding the connection part in the femur link 14 connected with the knee joint 12.

Figure 7:
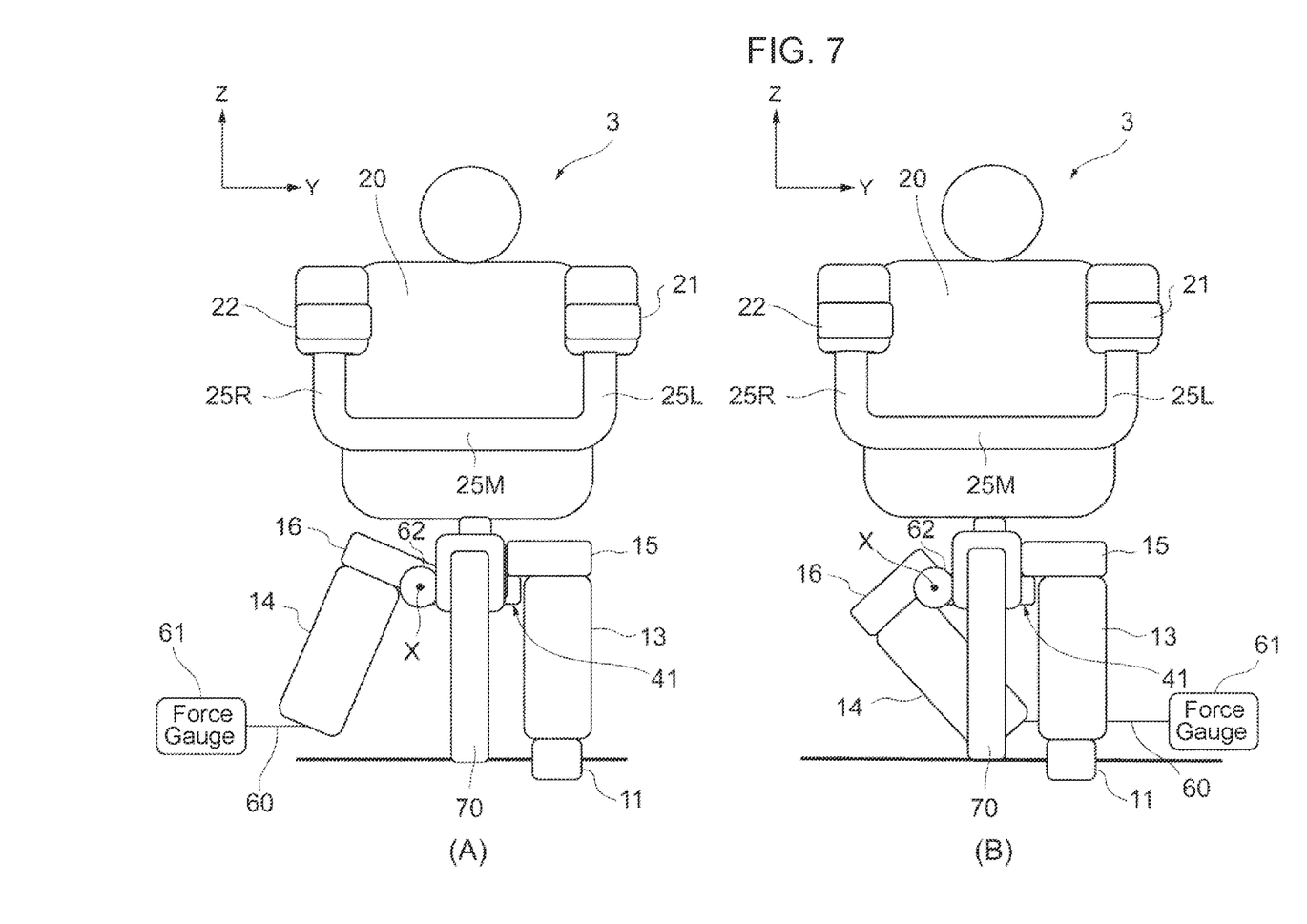
FIG. 7 is a schematic diagram for explaining performance evaluation of adduction/abduction range of motion by the performance evaluation apparatus according to the embodiment.

Referring to FIG. 7A and FIG. 7B, a force gauge (force component detecting unit) 61 is attached via a wire 60 to the connection part of the right-side femur link 14 with the knee joint 12 and detects a force component which acts on the axis line X in the rolling direction of the relevant hip joint 16. As another example of the force component detecting unit besides the force gauge 61, a 3-axis force torque sensor (not shown) may be provided on the rotation axis of the rolling direction of the right-side hip joint 16 to detect the force component on the basis of the torque which acts on the axis line of the relevant rolling direction.

Furthermore, an angle sensor (rotation angle detecting unit) 62 is provided on the rotation axis of the rolling direction of the right-side hip joint 16 and detects the rotation angle of the axis line X of the rolling direction relative to the trunk link 20. As another example of this rotation angle detecting unit besides the angle sensor 62, the rotation angle of the axis line X of the rolling direction may be detected on the basis of a measurement result by using an angle meter (not shown) from outside.

Incidentally, a rod-shaped support pole 70 can be mounted between the center of the right and left hip joints 15, 16 in the trunk link 20 and the base 2 in such a manner that the support pole 70 can be freely inserted; and when the connection of the right-side knee joint 12 is released and is moved away from the base 2, it is ensured that part of the load on the humanoid motion test unit 3 can be supported by the left-side leg (the knee joint 11, the femur link 13, and the hip joint 15) and the support pole 70.

Practically, while the wearable motion assistance device (see, for example, Japanese Patent Application No. 2014-198655) 50 for assisting the motions of the wearer's lower back part is mounted by securing the wearable motion assistance device 50 to both the femur links 13, 14 and either one or both of the trunk link 20 and the shoulder joints 21, 22 in the humanoid motion test unit 3, the control unit 10 evaluates the performance of the adduction/abduction range of motion by the wearable motion assistance device 50 as operated by the examiner on the basis of each detection result of the force gauge (the force component detecting unit) 61 and the angle sensor (the rotation angle detecting unit) 62.

Incidentally, an abduction motion range angle is required to exceed an angle of 15 degrees or more in consideration of followability with respect to opening the legs when the wearer actually performs the lift-up motion or sits down while using the wearable motion assistance device 50.

(4) Drive Transmission System for Estimation of Load on Lower Back Part

With the performance evaluation apparatus 1, a 6-axis force sensor 41 which serves as a load detecting unit for detecting the load applied to the relevant site is provided at a site corresponding to the wearer's lower back part in the trunk link 20 for the humanoid motion test unit 3.

Specifically speaking, the 6-axis force sensor 41 as the load detecting unit can find, in a simulated manner, a change rate indicative of how the assistance changes the load applied to the wearer's lower back part with the wearable motion assistance device 50 mounted thereon, by measuring a compressive force and bending moment applied to the site corresponding to the lower back part of the trunk link 20 for the humanoid motion test unit 3.

Since muscles of the back and their control are required in order to simulate compressive stress on a human's intervertebral disks, the testing apparatus would become complicated; however, almost the same effects can be obtained if how much the compressive force and the bending moment change depending on whether there is any assistance or not can be evaluated as described above.

Practically, while the wearable motion assistance device (see, for example, Japanese Patent Application No. 2014-198655) 50 for assisting the motions of the wearer's lower back part is mounted by securing the wearable motion assistance device 50 to both the femur links 13, 14 and either one or both of the trunk link 20 and the shoulder joints 21, 22 in the humanoid motion test unit 3, the control unit 10 estimates the load applied to the wearer's lower back part by the wearable motion assistance device 50 on the basis of the detection result of the 6-axis force sensor 41 as the load detecting unit according to the drive control of the first and second driving sources 5, 6.

Incidentally, as an evaluation method by estimating the load on the lower back part, a degree of reduction of the load on the lower back part can be found on the basis of the relationship between the compressive force in the Z-axis direction of the lower back part and the moment around Y-axis (pitch direction) of the lower back part.

(5) Motions According to this Embodiment

Regarding the above-described configuration, the wearable motion assistance device 50 for assisting motions of the wearer's lower back part is mounted on the performance evaluation apparatus 1 by securing the wearable motion assistance device 50 to both the femur links 13, 14 and either one or both of the trunk link 20 and the shoulder joints 21, 22 of the humanoid motion test unit 3.

The control unit 10 evaluates the performance of the assist force by the wearable motion assistance device 50 and judges whether or not a braking force of a predetermined level is generated upon the occurrence of a malfunction or a failure of the wearable motion assistance device 50, on the basis of the detection result of the torque detecting unit 40 according to the drive control of the first and second driving sources 5, 6.

As a result, when the wearable motion assistance device 50 does not generate the predetermined assist force for the sequence of motion patterns including the motions of lifting down an object, maintaining the posture, and lifting up the object or when the wearable motion assistance device 50 does not generate the braking force of the predetermined level upon the occurrence of any malfunction or failure, the wearable motion assistance device 50 can be evaluated as unacceptable.

Accordingly, with the performance evaluation apparatus 1, the first and second driving sources 5, 6 built in the base 2 can distribute and transmit the driving force to only one knee joint 12 and the other hip joint 15 as active joints from among the right and left femur links 13, 14 of the humanoid motion test unit 3, so that it is possible to reduce a transmission error occurrence probability as much as possible.

On the other hand, when both the knee joint and the hip joint which are connected to one femur link of the right and left femur links 13, 14 are used as the active joints, the installed status of belt driving inside the knee joint and the hip joint may become complicated and may possibly cause any defects by interfering with each other.

Subsequently, as a result of opening the legs or crossing one leg over the other by setting the right-side hip joint 16 as the center of the axis for the rolling direction while the examiner holding the right-side femur link 14 of the performance evaluation apparatus 1, the performance of the adduction/abduction range of motion by the wearable motion assistance device 50 is evaluated on the basis of each detection result of the force gauge (the force component detecting unit) 61 and the angle sensor (the rotation angle detecting unit) 62.

Accordingly, the performance evaluation apparatus 1 can easily evaluate not only the performance of the assist force for bending and extending of both the knee joints 11, 12 and both the hip joints 15, 16, but also the performance of the adduction/abduction range of motion of the right-side hip joint 16.

As a result, if the wearable motion assistance device 50 does not have the predetermined adduction/abduction range of motion, it can be evaluated as unacceptable.

Furthermore, with the performance evaluation apparatus 1, the control unit 10 estimates the load applied to the wearer's lower back part by the wearable motion assistance device 50 on the basis of the detection results of the 6-axis force sensor 41 as the load detecting unit, which are the compressive force and the bending moment at the site corresponding to the lower back part of the trunk link 20 according to the drive control of the first and second driving sources 5, 6.

As a result, it becomes possible to judge how much the load applied to the wearer's lower back part by the wearable motion assistance device has been reduced.

(6) Other Embodiments

Incidentally, this embodiment has been described about the case where the performance evaluation apparatus 1 is used to evaluate the assist force and the adduction/abduction range of motion of the wearable motion assistance device 50 and estimate the load applied to the wearer's lower back part; however, the present invention is not limited to this example and various other wearable motion assistance devices can be applied as long as the relevant wearable motion assistance device is a robot that is to be mounted by securing both the femoral parts and either one or both of the abdominal part and the shoulder parts of the wearer and assists the motions of the wearer's lower back part.

Regarding this wearable motion assistance device, it can be applied to any support purpose, whether for care support or for work support; and regarding its wearable style, even an abdominal wearing type or a shoulder wearing type can also be applied. Moreover, regarding the drive system, any type of drive systems, whether an electrically-driven type or a hydro-pneumatic type, can be applied; and regarding the motive power source, not only the internal motive power source, but also an external motive power source can be applied. Furthermore, regarding an input system, a wide variety of input systems such as a biological signal system, an interlocking phase estimation system, and a switch system can be applied.

Furthermore, this embodiment has been described about the case where: the arm links 25L, 25R which are configured to be connected and integrated in a substantially C-shape are supported via the shoulder joints 21, 22 respectively on the right and left upper sides of the trunk link 20 so that the arm links 25L, 25R can freely rotate; and the load with desired weight is applied to the central part 25M which is the site to connect both the arm links 25L, 25R. However, the present invention is not limited to this example and the shoulder joints and the arm links may not be freely rotatable and may be provided simply as weights.

Figure 8:
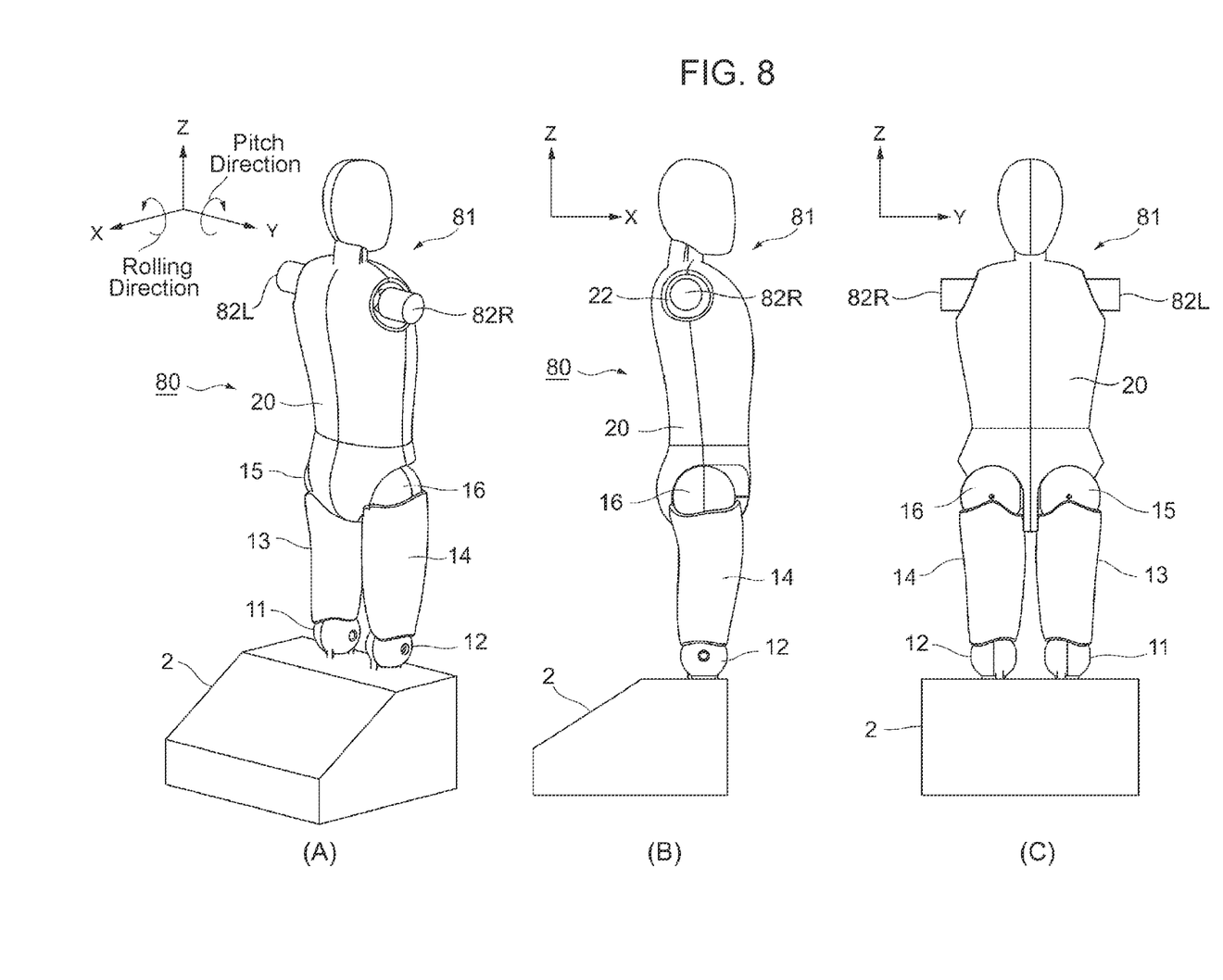
FIG. 8 shows a perspective view, a side view, and a front view which illustrate an appearance configuration of a performance evaluation apparatus according to another embodiment of the present invention.

Specifically speaking, referring to FIG. 8A to FIG. 8C where the same reference numerals are assigned to parts corresponding to those in FIG. 1A to FIG. 1C, a performance evaluation apparatus 80 has the same configuration as that of the performance evaluation apparatus 1 in FIG. 1, except the configuration of shoulder parts provided at right and left upper parts of the trunk link 20 for a humanoid motion test unit 81 is different.

The humanoid motion test unit 81 is equipped with a pair of substantially-cylindrical shoulder parts 82L, 82R which are composed of weights, each having the same desired weight, at both the right and left upper parts of the trunk link 20. As a result, the humanoid motion test unit 81 can be operated in a more stable manner than the case where both the arm links 25L, 25R which form the C-shape and to which the load is applied are supported via the shoulder joints 21, 22 in such a manner that the arm links 25L, 25R can freely rotate.

Specifically speaking, the shoulder parts 82L, 82R serving as the weights and both the arm links 25L, 25R with the load applied thereto do not have the same inertia moment; and the inertia moment with respect to the entire upper body in the former case serving as the weights is approximately 10% lower than the latter case. However, such difference cannot be achieved by the lift-up motion by a human with a degree of angular acceleration regarding which the above difference would cause a problem and, therefore, it is possible to ignore any error. Furthermore, antigravitational torque of the shoulder parts 82L, 82R as the weights is equal to that of both the arm links 25L, 25R with the load applied thereto when the arm links 25L, 25R hang vertically downward.

REFERENCE SIGNS LIST 1, 80: performance evaluation apparatus
2: base
3, 81: humanoid motion test unit
5: first driving source
6: second driving source
10: control unit
11, 12: knee joints
13, 14: femur links
15, 16: hip joints
20: trunk link
21, 22: shoulder joints
25L, 25R: arm links
25M: central part
30, 32, 33: belts
31: dependent roller
40: torque detecting unit
41: 6-axis force sensor
50: wearable motion assistance device
60: wire
61: force gauge
62: angle sensor
70: support pole
82L, 82R: shoulder parts

The invention claimed is:

1. A performance evaluation apparatus for a wearable motion assistance device to be mounted on a wearer by securing both femoral parts of the wearer and either one or both of an abdominal part and shoulder parts of the wearer to assist motions of a lower back part of the wearer, the performance evaluation apparatus comprising:
a base with first and second driving sources built therein;
right and left knee joints, each of which is connected between the base and a pair of femur links so that each knee joint can rotate freely in a pitch direction with a driving force of the first driving source transmitted to only either one of the knee joints;
right and left hip joints, each of which is connected between each femur link and a trunk link so that each hip joint can rotate freely in the pitch direction with a driving force of the second driving source transmitted to only either one of the hip joints;
a torque detecting unit that detects torque acting on an axis line of the pitch direction relative to the trunk link for each hip joint; and
a control unit that controls the driving forces by the first and second driving sources so that a posture of the trunk link and rotation angles of each hip joint and each knee joint virtually match motions of the lower back part of the wearer,
wherein the control unit evaluates performance of an assist force by the wearable motion assistance device on the basis of a detection result of the torque detecting unit according to drive control of the first and second driving sources in a state where the wearable motion assistance device is secured and mounted on both the femur links and the trunk link.

2. The performance evaluation apparatus for the wearable motion assistance device according to claim 1,
wherein in the state where the wearable motion assistance device is secured and mounted on both the femur links and the trunk link, the control unit judges whether or not a braking force of a predetermined level is generated upon the occurrence of a malfunction or a failure of the wearable motion assistance device, on the basis of a detection result of the torque detecting unit in accordance with drive control of the first and second driving sources.

3. The performance evaluation apparatus for the wearable motion assistance device according to claim 1,
wherein at least one of the respective hip joints can rotate in a rolling direction relative to the femur link and the connection with the base at the femur link can be released;
wherein the performance evaluation apparatus further includes, within the apparatus or as separate units:
a force component detecting unit that detects a force component acting on an axis line of the rolling direction of the hip joint; and
a rotation angle detecting unit that detects a rotation angle of the axis line of the rolling direction of the hip joint; and
wherein when an external force is applied in the rolling direction of the femur link in the state where the wearable motion assistance device is secured and mounted on both the femur links and the trunk link, the control unit evaluates performance of an adduction/abduction range of motion by the wearable motion assistance device, on the basis of each detection result of the force component detecting unit and the rotation angle detecting unit.

4. The performance evaluation apparatus for the wearable motion assistance device according to claim 1,
further comprising a load detecting unit that is provided at a site in the trunk link corresponding to the lower back part of the wearer and detects a load applied to the site,
wherein in the state where the wearable motion assistance device is secured and mounted on both the femur links and the trunk link, the control unit estimates the load applied to the lower back part of the wearer by the wearable motion assistance device on the basis of a detection result of the load detecting unit in accordance with drive control of the first and second driving sources.

5. The performance evaluation apparatus for the wearable motion assistance device according to claim 1,
further comprising a shoulder joint that is connected between the trunk link and a pair of arm links and is attached to the trunk link in such a manner that the shoulder joint can freely rotate, wherein when a load with desired weight is applied at a predetermined position of the arm link, the load is supported via the shoulder joint in a freely rotatable manner.

6. The performance evaluation apparatus for the wearable motion assistance device according to claim 1,
further comprising a pair of shoulder parts, each of which is composed of a weight having the same desired weight, on both upper sides of the trunk link.

7. A performance evaluation method for a wearable motion assistance device to be mounted on a wearer by securing both femoral parts of the wearer and either one or both of an abdominal part and shoulder parts of the wearer to assist motions of a lower back part of the wearer,
wherein the following are included: a base with first and second driving sources built therein; right and left knee joints, each of which is connected between the base and a pair of femur links so that each knee joint can rotate freely in a pitch direction with a driving force of the first driving source transmitted to only either one of the knee joints; and right and left hip joints, each of which is connected between each femur link and a trunk link so that each hip joint can rotate freely in the pitch direction with a driving force of the second driving source transmitted to only either one of the hip joints; and
wherein the performance evaluation method comprising, in a state where the wearable motion assistance device is secured and mounted on both the femur links and the trunk link:
detecting torque acting on an axis line of the pitch direction relative to the trunk link for each hip joint while controlling the driving forces by the first and second driving sources so that a posture of the trunk link and rotation angles of each hip joint and each knee joint virtually match motions of the lower back part of the wearer; and
evaluating performance of an assist force by the wearable motion assistance device on the basis of a detection result of the torque according to drive control of the first and second driving sources.

8. The performance evaluation method for the wearable motion assistance device according to claim 7,
wherein in the state where the wearable motion assistance device is secured and mounted on both the femur links and the trunk link, whether or not a braking force of a predetermined level is generated upon the occurrence of a malfunction or a failure of the wearable motion assistance device is judged on the basis of the detection result of the torque detecting unit in accordance with drive control of the first and second driving sources.

9. The performance evaluation method for the wearable motion assistance device according to claim 7,
wherein at least one of the respective hip joints can rotate in a rolling direction relative to the femur link and the connection with the base at the femur link can be released; and
wherein when an external force is applied in the rolling direction of the femur link in the state where the wearable motion assistance device is secured and mounted on both the femur links and the trunk link, performance of an adduction/abduction range of motion by the wearable motion assistance device is evaluated on the basis of a force component acting on an axis line of the rolling direction of the hip joint and a rotation angle of the axis line.

10. The performance evaluation method for the wearable motion assistance device according to claim 7,
wherein a load applied to a site in the trunk link corresponding to the lower back part of the wearer is detected; and
wherein in the state where the wearable motion assistance device is secured and mounted on both the femur links and the trunk link, the load applied to the lower back part of the wearer by the wearable motion assistance device is estimated on the basis of a detection result of the load in accordance with drive control of the first and second driving sources.

11. The performance evaluation method for the wearable motion assistance device according to claim 7,
wherein a shoulder joint that is connected between the trunk link and a pair of arm links and is attached to the trunk link in such a manner that the shoulder joint can freely rotate is further included; and
wherein when a load with desired weight is applied at a predetermined position of the arm link, the load is supported via the shoulder joint in a freely rotatable manner.

12. The performance evaluation method for the wearable motion assistance device according to claim 7,
wherein a pair of shoulder parts, each of which is composed of a weight having the same desired weight, is further included on both upper sides of the trunk link.

* * * * *